(12) United States Patent
Dell'orco et al.

(10) Patent No.: US 7,754,733 B2
(45) Date of Patent: Jul. 13, 2010

(54) CRYSTALLINE TOPOTECAN HYDROCHLORIDE PRODUCT AND PROCESS FOR MAKING THE SAME

(75) Inventors: Philip C. Dell'orco, King of Prussia, PA (US); Ann Marie Diederich, King of Prussia, PA (US); Qiaogong Su, King of Prussia, PA (US); Jeffery Lee Wood, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 10/578,660

(22) PCT Filed: Nov. 12, 2004

(86) PCT No.: PCT/US2004/037626

§ 371 (c)(1),
(2), (4) Date: May 9, 2006

(87) PCT Pub. No.: WO2005/046608

PCT Pub. Date: May 26, 2005

(65) Prior Publication Data

US 2007/0117832 A1    May 24, 2007

Related U.S. Application Data

(60) Provisional application No. 60/524,574, filed on Nov. 24, 2003, provisional application No. 60/519,160, filed on Nov. 12, 2003.

(51) Int. Cl.
*C07D 491/22* (2006.01)
*A61K 31/4745* (2006.01)

(52) U.S. Cl. ........................................ 514/283; 546/48

(58) Field of Classification Search ................. 514/283; 546/48

See application file for complete search history.

(56) References Cited

U.S. PATENT DOCUMENTS

| 5,004,758 A | 4/1991 | Boehm et al. ............... 514/283 |
| 5,734,056 A | 3/1998 | Burk ........................... 546/48 |
| 2007/0105885 A1 | 5/2007 | Pathi et al. .................. 514/283 |
| 2007/0149783 A1 | 6/2007 | Palle et al. .................... 546/51 |
| 2008/0269493 A1 | 10/2008 | Hu et al. ...................... 546/48 |
| 2009/0192184 A1 | 7/2009 | Pozzi et al. .................. 514/283 |

FOREIGN PATENT DOCUMENTS

| WO | WO 03/027118 A1 | 4/2003 |
| WO | WO 2007/042799 | 4/2007 |
| WO | WO 2008/130534 | 10/2008 |

OTHER PUBLICATIONS

Vogt et al. *Journal of Pharmaceutical and Biomedical Analysis*, 40(5): 1080-1088 (2006).
Product Data Sheet for Topotecan Hydrochloride (Oct. 9, 2002) http://search.cosmobio.co.jp/cosmo_search_p/search_gate2/docs/CBC_/614800.20040716.pdf.
Calbiochem biologics, vol. 28, No. 1 (2002) http://www.emdbiosciences.com/SharedImages/TechnicalLiterature/1_Biol28_1_np.pdf.
Orange Book listing for Topotecan Hydrochloride, 2008.
PDR Entry for: HYCAMTIN®, 2006.

*Primary Examiner*—Charanjit S Aulakh
(74) *Attorney, Agent, or Firm*—Kathryn L. Sieburth; Lorraine Ling

(57) ABSTRACT

Disclosed is a novel crystalline form of topotecan monohydrochloride pentahydrate, which is a pentahydrate of 10-[(dimethylamino)methyl]4-ethyl-4,9-dihydroxy-1H-pyrano [3',4':6,7]indolizino[1,2-b]quinoline-3,14(4H, 12H)dione monohydrochloride, corresponding pharmaceutical compositions, methods preparation and/or use thereof to treat antiviral and/or cancer related diseases.

27 Claims, 3 Drawing Sheets

CRYSTALLINE TOPOTECAN HYDROCHLORIDE PRODUCT AND PROCESS FOR MAKING THE SAME

This application is a 371 of International Application No. PCT/US2004/037626, filed 12 Nov. 2004, which claims priority of U.S. Provisional Application Nos. 60/524,574, filed 24 Nov. 2003 and 60/519,160, filed 12 Nov. 2003.

FIELD OF THE INVENTION

The present invention relates to a novel crystalline form of topotecan monohydrochloride pentahydrate, corresponding pharmaceutical compositions, methods of preparation and/or use thereof to treat anti-viral and/or cancer-related diseases.

BACKGROUND OF THE INVENTION

A fundamental step to cellular DNA replication and transcription processes is associated with the separation of DNA helical strands. DNA helical structure of eukaryotic cells dictate specific topological properties which may lead to problems that a cellular apparatus must resolve in order to use genetic material as a template for cellular replication processes. Eukaryotic DNA strands, organized into chromatin by chromosomal proteins, are constrained such that those strands cannot unwind without the aid of topology altering enzymes. In light of this, it has long been recognized that advancement of a transcription or replication complex along a DNA helix would be facilitated by a swivel point that would relieve conformational torsional strain generated during such processes.

Topoisomerases are important enzyme components in cellular functions capable of altering DNA topology in eukaryotic cells and cell proliferation processes. Topoisomerases alter the linking number of DNA (i.e., equal to the number of times that a DNA strand winds in right handed helical axis direction) by catalyzing a three step process: the cleavage of one or both strands of DNA, the passage of a segment of DNA through such break(s), and the resealing of the DNA break.

Two topoisomerase classes have been associated with eukaryotic cells: Type I topoisomerase and type II topoisomerase. Both topoisomerases type I and type II play important roles in DNA replication, transcription, and recombination. In general, inhibition of topoisomerase I has been the major target of oncologic, anti-neoplastic, anti-viral agents, etc. Inhibition of topoisomerase II is the major target of important commercial oncolytic agents (e.g., etoposide, doxorubicin and mitoxantrone) as well as other oncolytic agents still undergoing development.

An example of a class of DNA topoisomerase I inhibiting compounds include camptothecin and its corresponding analog or congener derivatives. Camptothecin is a water-insoluble, cytotoxic alkaloid produced by plants, such as Camptotheca accuminata trees indigenous to China and Nothapodytes foetida trees indigenous to India. Camptothecins generally (such as topotecan) are discussed in Cancer Chemotherapy and Biotherapy (see, pp. 463-484; 2nd edition, Eds. Bruce A. Chabner and Dan L. Longo, Lippincott-Raven Publishers, Philadelphia, 1996). Examples of camptothecin analog derivatives include topotecan, irinotecan, and 9-aminocamptothecin.

U.S. Pat. No. 5,004,758 discloses topotecan, (S)-10-[(dimethylamino)methyl]-4-ethyl-4,9-dihydroxy-1H-pyrano[3',4': 6,7]indolizino[1,2-b]quinoline-3,14(4H,12H)dione monohydrochloride (also known as 9-dimethylaminomethyl-10-hydroxycamptothecin, etc.), as depicted by the following chemical structure:

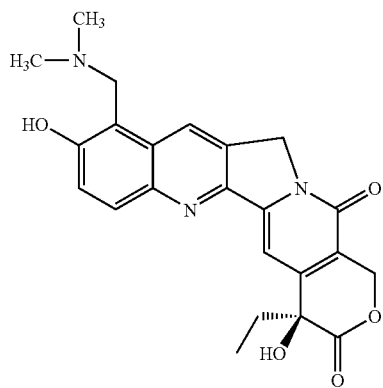

(S) - Topotecan

Topotecan also is listed in The Merck Index (see 12th Ed., monograph no. 9687, Merck & Co., Inc., 1996). Clinical tests have shown that topotecan demonstrates efficacy against several solid tumor cancers, particularly ovarian cancer, esophageal cancer, and non-small cell lung carcinoma in humans.

Hycamtin® (sold by GlaxoSmithKline, Brentford, UK), which contains topotecan hydrochloride, is formulated as a lyophilized mixture, suitable for intravenous administration after reconstitution. Typically, this product is administered by medical professionals in a hospital, clinic or doctor's office setting. This dosing requires patients to travel to such facilities, sometimes daily, for treatment. It would be desirable to develop a pharmaceutical form of topotecan hydrochloride that could be readily and safely manufactured and would be useful in the preparation of a pharmaceutical composition that could be administrable by patients in any setting, e.g. at home. Generally, such self-administrable pharmaceutical forms are solid, orally administrable forms.

SUMMARY OF THE INVENTION

The present invention relates to a compound which is a topotecan monohydrochloride pentahydrate characterized by substantially the same X-ray powder diffraction (XRPD) pattern as FIG. 1.

The present invention also relates to a compound which is a topotecan monohydrochloride pentahydrate characterized by an X-ray powder diffraction (XRPD) pattern having peak positions at 4.5±0.1 (° 2θ), 6.4±0.1 (° 2θ), 7.1±0.1 (° 2θ), 9.0±0.1 (° 2θ), 10.1±0.1 (° 2θ), 11.5±0.1 (° 2θ), 12.6±0.1 (° 2θ), 13.1±0.1 (° 2θ), 14.1±0.1 (° 2θ), 15.5±0.1 (° 2θ), 17.9±0.1 (° 2θ), 18.7±0.1 (° 2θ), 20.0±0.1 (° 2θ), 20.3±0.1 (° 2θ), 21.1±0.1 (° 2θ), 21.8±0.1 (° 2θ), 23.0±0.1 (° 2θ), 24.8±0.1 (° 2θ), 25.6±0.1 (° 2θ), 26.6±0.1 (° 2θ), 27.2±0.1 (° 2θ), and 28.9±0.1 (° 2θ).

The present invention relates to a compound, which is topotecan monohydrochloride pentahydrate characterized by a solid state FT-IR (KBr) spectrum that provides an inverse second derivative spectrum for the spectral region of 1800 $cm^{-1}$ to 1500 $cm^{-1}$ that is substantially the same as FIG. 3.

This invention further relates to a compound, which is topotecan monohydrochloride pentahydrate, characterized by a second derivative solid state FT-IR (KBr) spectrum having peaks at 1754±2 $cm^{-1}$, 1745±2 $cm^{-1}$, 1740±2 $cm^{-1}$, 1658±2 $cm^{-1}$, 1649±2 $cm^{-1}$, 1596±2 $cm^{-1}$, 1584±2 $cm^{-1}$, and 1507±2 $cm^{-1}$.

The present invention also relates to pharmaceutical compositions, which comprise the topotecan monohydrochloride pentahydrate of this invention. The compositions of this invention further comprise one or more pharmaceutically acceptable carriers, including adjuvants, diluents, excipients, etc.

This invention relates to a process for preparing the topotecan monohydrochloride pentahydrate of this invention, wherein the process comprises the steps of: [a] forming an aqueous organic solvent mixture containing topotecan monohydrochloride; [b] recrystallizing the topotecan monohydrochloride from and/or slurrying the topotecan monohydrochloride with the aqueous organic solvent mixture to precipitate and/or form the topotecan monohydrochloride pentahydrate product; and [c] collecting, by filtration, the topotecan monohydrochloride pentahydrate.

The present invention further relates to a method of treating cancer which comprises administering to a subject in need thereof an effective amount of the topotecan monohydrochloride pentahydrate of this invention.

The present invention relates to a method of treating cancer which comprises administering to a subject in need thereof an effective amount of a pharmaceutical composition which comprises the topotecan monohydrochloride pentahydrate of this invention.

The present invention further provides the topotecan monohydrochloride pentahydrate of this invention for use in therapy.

The present invention also provides the use of the topotecan monohydrochloride pentahydrate of this invention in the preparation of a medicament for the treatment of cancer and the use of the topotecan monohydrochloride pentahydrate of this invention in the preparation of a medicament for ameliorating one or more of the symptoms associated with cancer.

DETAILED DESCRIPTION OF THE INVENTION

Figure 1:
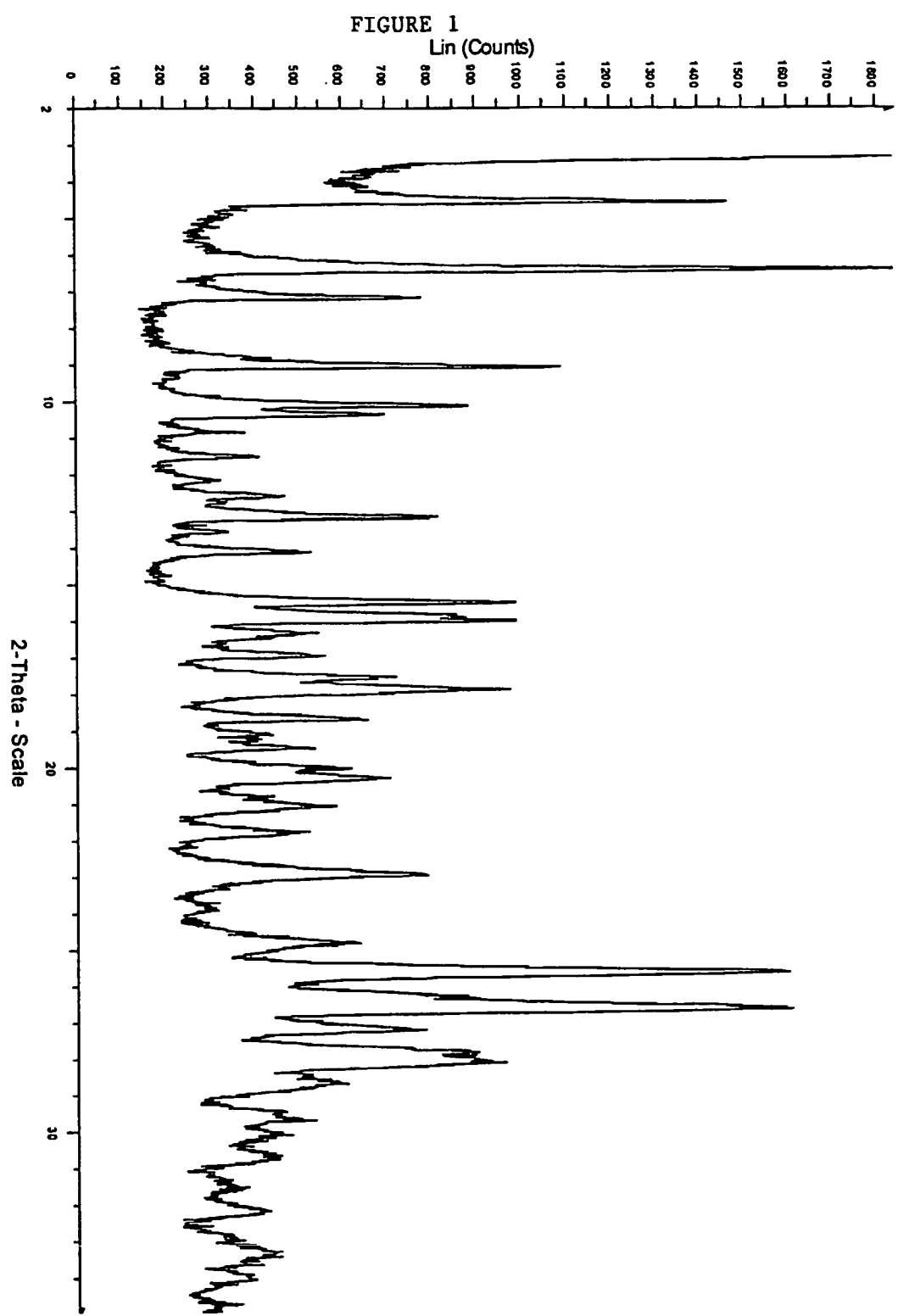
FIG. 1 is an x-ray powder diffractogram of a topotecan monohydrochloride pentahydrate polymorphic form depicting characteristic peaks substantially identified from the region 0° degrees 2-heta (° 2θ) to 35° degrees 2-theta (° 2θ)

Topotecan (salts, hydrates, and/or solvates thereof) suitable for use in the present invention, which include starting materials (i.e., such as topotecan monohydrochloride), intermediates or products, etc. are prepared as described herein, and/or by the application or adaptation of known methods, which may be methods used heretofore or described in the literature.

U.S. Pat. No. 5,004,758 discloses water soluble camptothecin analogs, which includes topotecan (9-dimethylaminomethyl-10-hydroxycamptothecin), preferably (S)-topotecan, most preferably as the hydrochloride salt. U.S. Pat. No. 5,734,056 discloses water soluble camptothecin compound analogs (which include topotecan), a process for the preparation of such analogs and/or intermediates useful therein.

U.S. Pat. No. 5,155,225 generally discloses methods for making pyrano[3',4':6,7]indolizino-[1,2-B]quinolinones. U.S. Pat. Nos. 5,405,963, 5,468,859, 5,541,329, 5,700,939, 5,663,177, and 5,670,500 disclose general processes for asymmetric total synthesis of camptothecin analogues and/or corresponding compound intermediates, pharmaceutical compositions, and/or methods of making and/or use of analogs.

U.S. Pat. Nos. 5,674,872 and 5,756,512 disclose methods for the treatment of ovarian cancer and non-small lung carcinoma, respectively, which comprise administration of an effective amount of a compound of the water soluble camptothecin analog class, which includes topotecan. U.S. Pat. No. 5,633,016 discloses combination chemotherapy related to the use of a camptothecin analog class compound (i.e., topotecan) and a platinum coordination compound. U.S. Pat. No. 6,582,689 discloses compositions, which comprise potentiators, an interferon-gamma-inducing factor (IGIF; such as IL-18), in combination with a chemotherapeutic agent (which may include topotecan), processes for making such compositions, the use of such compositions to inhibit the growth of tumors or cancerous cells, and/or for prevention and/or treatment of cancer in mammals.

Topotecan monohydrochloride, and solvates (particularly, hydrates) thereof, exhibit polymorphism. As conventionally understood in the art, polymorphism is defined as an ability of a compound to crystallize as more than one distinct crystalline or "polymorphic" species. A polymorph is defined as a solid crystalline phase of a compound with at least two different arrangements or polymorphic forms of that compound molecule in the solid state.

Polymorphic forms of any given compound are defined by the same chemical formula and/or composition but are as distinct in chemical structure as crystalline structures of two different chemical compounds. Such compounds may differ in packing, geometrical arrangement of respective crystalline lattices, etc. Accordingly, the chemical and/or physical properties or characteristics vary with each distinct polymorphic form, which may include variations in solubility, melting point, density, hardness. crystal shape, optical and electrical properties, vapor pressure, stability, etc.

Polymorphic forms of any given compound may be distinguished from each other using different characterization or identification techniques. For example, conventional organic chemistry identification techniques may be used to distinguish different polymorphic forms. Such identification techniques may include, but are not limited to: Infrared Spectroscopy (IR), Nuclear Magnetic Resonance (NMR) (i.e., such as Proton Magnetic Resonance ($^1$H NMR), $^{13}$C Nuclear Magnetic Resonance ($^{13}$C NMR), $^{31}$P Nuclear Magnetic Resonance ($^{31}$P NMR)), Electron Microscopy, X-Ray Powder Diffraction (XRPD), Optical Crystallography, Differential Scanning Calorimetry (DSC), Differential Thermal Analysis, Dilatometry, etc.

The novel topotecan monohydrochloride pentahydrate of this invention is a specific crystalline polymorphic form of the pentahydrate of 10-[(dimethylamino)methyl]-4-ethyl-4,9-dihydroxy-1H-pyrano[3',4':6,7]indolizino[1,2-b]quinoline-3, 14(4H,12H)dione monohydrochloride (or 9dimethylaminomethyl-10-hydroxycamptothecin monohydrochloride pentahydrate). This topotecan monohydrochloride pentahydrate can be readily isolated, and displays uniformity, reproducibility, ease and safety of handling in manufacture, and stability on isolation and drying.

The topotecan monohydrochloride pentahydrate of this invention is characterized by substantially the same XRPD pattern as depicted in FIG. 1. The XRPD pattern of FIG. 1 is expressed in terms of 2-theta angles and obtained with a diffractometer using copper Kα X-radiation. It will be understood by those skilled in the art that an XRPD pattern will be considered to be substantially the same as the XRPD pattern of FIG. 1 if the difference in peak positions of the XRPD patterns are not more than ±0.1 (° 2θ).

The topotecan monohydrochloride pentahydrate is further characterized by an XRPD pattern having peak positions at 4.5±0.1 (° 2θ), 6.4±0.1 (° 2θ), 7.1±0.1 (° 2θ), 9.0±0.1 (° 2θ), 10.1±0.1 (° 2θ), 11.5±0.1 (° 2θ), 12.6±0.1 (° 2θ) 13.1±0.1 (° 2θ), 14.1±0.1 (° 2θ), 15.5±0.1 (° 2θ), 17.9±0.1 (° 2θ), 18.7±0.1 (° 2θ) 20.0±0.1 (° 2θ), 20.3±0.1 (° 2θ), 21.1±0.1 (° 2θ), 21.8±0.1 (° 2θ), 23.0±0.1 (° 2θ) 24.8±0.1 (° 2θ), 25.6±0.1 (° 2θ), 26.6±0.1 (° 2θ), 27.2±0.1 (° 2θ), and 28.9±0.1 (° 2θ). The location (° 2θ values) of these peaks was obtained from an XRPD pattern expressed in terms of 2-theta angles and obtained with a diffractometer using copper Kα X-radiation.

Figure 3:
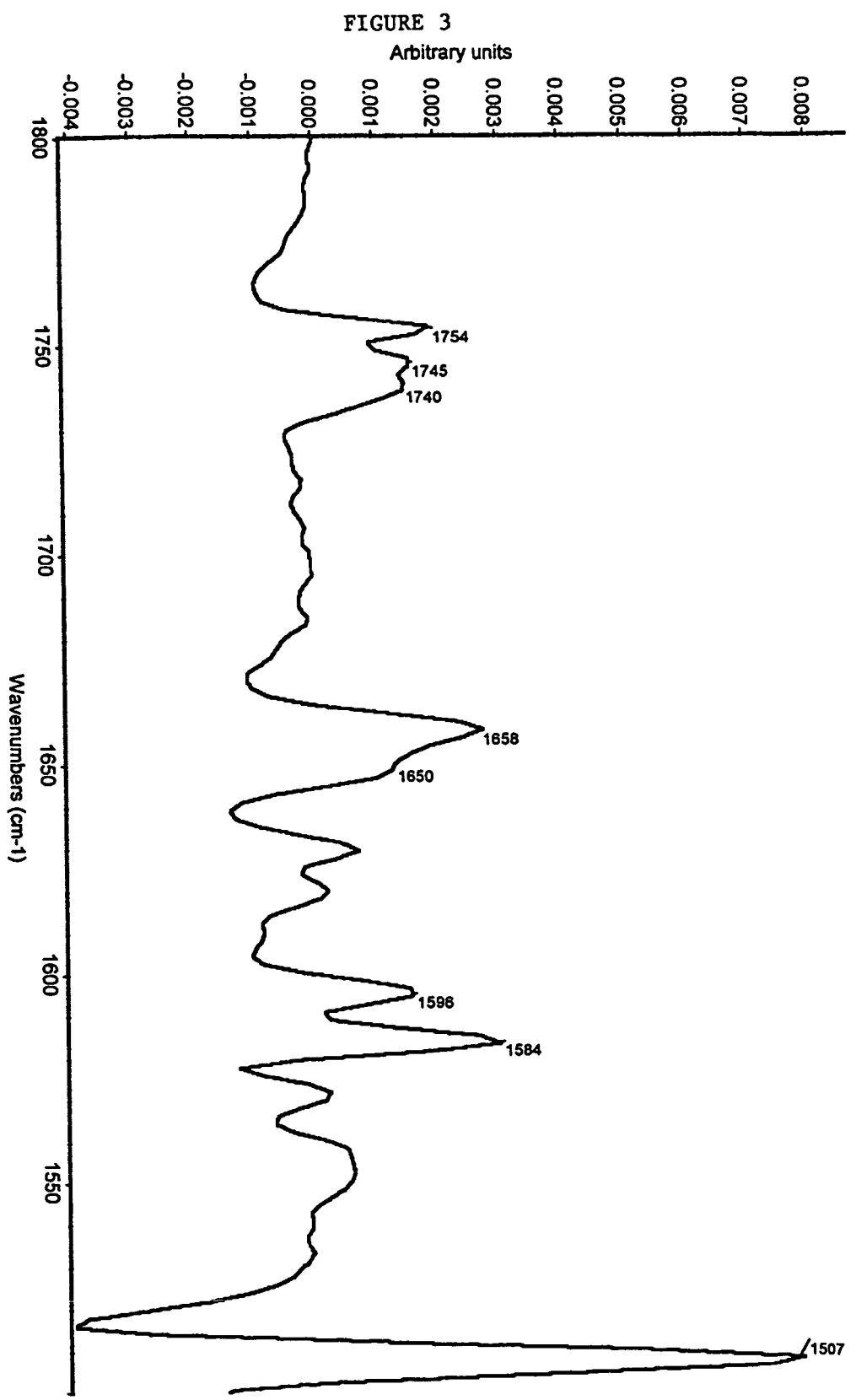
FIG. 3 is an inverse second derivative spectrum of the 1800 $cm^{-1}$ to 1500 $cm^{-1}$ region of the FT-IR (KBr) spectrum of a topotecan monohydrochloride pentahydrate polymorphic form.

The topotecan monohydrochloride pentahydrate of this invention is also characterized by substantially the same inverse second derivative solid state FT-IR (KBr) spectrum for the spectral region of 1800 cm$^{-1}$ to 1500 cm$^{-1}$ as FIG. 3. It will be understood by those skilled in the art that an inverse second derivative FT-IR (KBr) spectrum from 1800 to 1500 cm$^{-1}$ will be considered to be substantially the same as the FT-IR (KBr) spectrum of FIG. 3 if the difference in peak positions of the FT-IR spectra are not more than ±2 cm$^{-1}$.

The topotecan monohydrochloride pentahydrate of this invention is further characterized by a second derivative solid state FT-IR (KBr) spectrum having peaks at 1754±2 cm$^{-1}$, 1745±2 cm$^{-1}$, 1740±2 cm$^{-1}$, 1658±2 cm$^{-1}$, 1649±2 cm$^{-1}$, 1596±2 cm$^{-1}$, 1584±2 cm$^{-1}$, and 1507±2 cm$^{-1}$.

The topotecan monohydrochloride pentahydrate of this invention may have a water content range between from about ≧10% w/w % to about ≦17 w/w %. The water content associated with the topotecan monohydrochloride pentahydrate may also be in a range of about 3.5 wt % to about 20 wt %. Specifically, the topotecan monohydrochloride pentahydrate of this invention may have a water content in a range of about 10.5 wt % to about 16.5 wt %.

The topotecan monohydrochloride pentahydrate product of this invention can exist in the same crystal form whether it has 3, 4 or 5 water molecules associated with the crystal form (that is, each of the trihydrate, tetrahydrate, and pentahydrate of the topotecan monohydrochloride of this invention provides substantially the same XRPD pattern as that of FIG. 1). The topotecan monohydrochloride pentahydrate product of the present invention has a crystalline lattice structure which incorporates three crystal lattice bound water molecules therein (the trihydrate state). The topotecan monohydrochloride pentahydrate product may also incorporate two coordinatively bound, labile channel water molecules; their removal from the lattice to form the trihydrate state does not affect the crystallinity of the material as measured by X-ray powder diffraction and infrared spectroscopy techniques. If the topotecan monohydrochloride pentahydrate product is dried to the trihydrate state, then permitted to absorb additional water molecules (e.g., from humid air), it will take up two channel water molecules. If the topotecan monohydrochloride pentahydrate product is incompletely dried, analysis may indicate that the product contains more than five water molecules. However, of these, three will be crystal lattice bound water molecules, two will be channel water molecules, and any additional water will be surface water molecules (bound to the surface of the crystal, but otherwise not affecting the crystallinity of the topotecan monohydrochloride product). The topotecan monohydrochloride product of this invention is described as a pentahydrate because, in environments of about 40 to about 90% relative humidity, this product will equilibrate to contain 5 water molecules.

This invention also relates to a process for preparing the topotecan monohydrochloride pentahydrate product of this invention, where the process comprises the steps of:

[a] forming an aqueous organic solvent mixture containing topotecan monohydrochloride;

[b] recrystallizing the topotecan monohydrochloride from and/or slurrying the topotecan monohydrochloride with the aqueous organic solvent mixture to precipitate and/or form the topotecan monohydrochloride pentahydrate product; and

[c] collecting, by filtration, the topotecan monohydrochloride pentahydrate product.

Suitable organic solvents for use in the processes of the present invention to form aqueous organic solvent mixtures include, but are not limited to, acetone, tetrahydrofuran, methanol, ethanol, n-propanol, isopropanol, dimethylsulfoxide, and N,N-dimethylformamide, and mixtures thereof. Other solvents that may be useful in the process of this invention include ethyl acetate, acetonitrile and dichloromethane, and/or mixtures thereof and/or mixtures with one or more of the above-noted organic solvents. Particularly useful solvents include acetone, tetrahydrofuran, and n-propanol, more particularly, acetone and tetrahydrofuran.

The "aqueous" portion of the aqueous organic solvent mixture is an aqueous solvent that may be water or an aqueous mineral acid solution. Advantageously, the aqueous organic solvent mixture comprises an aqueous mineral acid solution. In one embodiment, the mineral acid solution is an aqueous hydrochloric acid solution (aqueous HCl), wherein the acid solution is 0.05 N aqueous HCl.

For the recrystallization processes identified in step [b], the aqueous organic solvent solution mixture may comprise a mixture of an organic solvent and an aqueous solvent in a ratio (v/v) from about 1.5:1 to about 3:1, wherein the aqueous solvent is preferably an aqueous mineral acid solution. A preferable range for the ratio (v/v) of organic solvent to aqueous solvent, for the recrystallization process, is from about 1.5:1 to about 2:1.

For the slurrying processes identified in step [b], an aqueous organic solvent solution mixture useful in an aforementioned process of the present invention may have an organic solvent to aqueous solvent ratio (v/v) from about 2:1 to about 8:1. A preferable organic solvent to aqueous solvent ratio, for the slurrying process, is about 8:1.

The aqueous organic solvent solution mixture is used in the process of this invention such that the aq. organic solvent solution mixture (volume/milliliters) to topotecan monohydrochloride (weight/grams) ratio is from about 7:1 to about 13:1. A preferable range useful for the recrystallization process is an aq. organic solvent solution mixture (volume/milliliters) to topotecan monohydrochloride (weight/grams) ratio of from about 10.6:1 to about 13:1, more preferably 12:1. A preferable range useful for the slurrying process is an aq. organic solvent solution mixture (volume/milliliters) to topotecan monohydrochloride (weight/grams) ratio of from about 7:1 to about 12:1, more preferably 12:1.

The topotecan monohydrochloride pentahydrate product may be dried after filtration to remove any remaining traces of the recrystallization solvents. The drying process should be conducted in a manner that does not reduce the water/topotecan stoichiometry to less than 3 mol water/1 mol topotecan HCl; that is, the water/topotecan stoichiometry of the topotecan monohydrochloride pentahydrate product is at least 3 mol water/1 mol topotecan HCl. Generally, the topotecan monohydrochloride pentahydrate product obtained by the process of this invention should not be dried at pressures of less than about 30 mm Hg or at temperatures greater than about 37° C.

In one embodiment of the process of this invention, the topotecan monohydrochloride pentahydrate of this invention may be prepared by first dissolving topotecan monohydrochloride in a heated aqueous organic solvent solution mixture. In a specific embodiment of this invention, the heated aqueous organic solvent solution mixture is a mixture of acetone and 0.05 N aqueous hydrochloric acid heated to a temperature of about 58° C. and the ratio of the volume of acetone to aqueous hydrochloric acid is about 2:1. Crystallization/recrystallization of the topotecan monohydrochloride pentahydrate from the heated solution may be accomplished by cooling the solution, filtering the resulting recrystallized topotecan monohydrochloride pentahydrate product and drying. Advantageously, the cooling process may be conducted by cooling the heated topotecan monohydrochloride solution with stirring. The cooling rate should generally be in the range of about 0.1° C./min to about 1° C./min. In a specific embodiment, the cooling rate is about 0.25° C./min. In the crystallization (recrystallization) process, the solution/mixture may be cooled to a temperature of about room temperature to about 0° C. After filtering the topotecan monohydrochloride pentahydrate product from the recrystallization solvent, the collected/filtered product may be dried to remove any remaining traces of the crystallization/recrystallization solvents. Examples of useful drying conditions include drying at 20-25° C. at 165-300 mm Hg for up to 14 days or for 28-32° C. at 150-200 mm Hg for >24 hours, with a nitrogen bleed.

This invention is also directed to pharmaceutical compositions comprising the topotecan monohydrochloride pentahydrate of this invention. The compositions of this invention further comprise one or more pharmaceutically acceptable carriers. If desired, the pharmaceutical compositions of this invention may further comprise other active ingredients. The pharmaceutical compositions of the present invention may also include other ingredients such as stabilizers, antioxidants, preservatives, lubricants, suspending agents, viscosity modifiers and the like, provided that the additional ingredients do not have a detrimental effect on the therapeutic action of the instant compositions. The forms of the pharmaceutical compositions of the present invention include either a solid form (i.e., tablets, capsules, powders, etc.) or a liquid form (i.e., suspensions, or emulsions, etc.) wherein the topotecan monohydrochloride pentahydrate is present in the pharmaceutical composition in the crystalline form defined hereinabove. In general, the pharmaceutical compositions of the present invention are prepared using conventional art known materials and techniques, which may include, but are not limited to mixing, blending and the like. The percentage of the topotecan monohydrochloride pentahydrate in pharmaceutical compositions of the present invention may be varied to provide a desired amount of active compound in such therapeutically useful compositions, such that a suitable dosage will be obtained.

The topotecan monohydrochloride pentahydrate and/or the pharmaceutical compositions of the present invention may be useful in treatment methods providing anti-viral and/or anti-neoplastic activity. For example, various cancers treatable using the topotecan monohydrochloride pentahydrate and/or pharmaceutical compositions of the present invention include solid tumor types (i.e., which may include, but are not limited to ovarian cancer, breast cancer, endometrial cancer, esophageal cancer, small and non-small cell lung cancer, cervical cancer, colorectal cancer, neuroblastomas, glioma and the like) and non-solid tumor types (i.e., which may include, but are not limited to myelodysplastic syndrome, acute myelogenous leukemia, chronic myelomonocytic leukemia and the like) in mammals, such as humans.

The topotecan monohydrochloride pentahydrate and/or pharmaceutical compositions of the present invention have both a human and a veterinary utility. If a veterinary use is intended, the topotecan monohydrochloride pentahydrate and/or pharmaceutical compositions of the present invention may be formulated with a carrier that may be a liquid, or spray, or may be formulated in a solid, non-degradable or degradable form for insertion in the rumen. Selected carriers, such as those described herein, may be employed to prepare compositions acceptable or adaptable for veterinary use.

Accordingly, this invention relates to a method of treating cancer, which comprises administering to a subject in need thereof an effective amount of the topotecan monohydrochloride pentahydrate of this invention. This invention also relates to a method of treating cancer which comprises administering to a subject in need thereof an effective amount of a pharmaceutical composition which comprises an effective amount of the topotecan monohydrochloride pentahydrate of this invention This invention also relates to a method of using the topotecan monohydrochloride pentahydrate of this invention and/or a pharmaceutical composition comprising the same as a palliative to ameliorate one or more of the symptoms associated with cancer, which comprises administering to a subject in need thereof an effective amount of the topotecan monohydrochloride pentahydrate of this invention and/or a pharmaceutical composition comprising the same. The amelioration of symptoms associated with cancer can improve the quality of life for patients with cancer, particularly lung cancer. Examples of cancer symptoms that can be improved by treatment with topotecan monohydrochloride pentahydrate and/or pharmaceutical compositions comprising the same include, but are not limited to, pain, fatigue, insomnia, interference with daily activity and disease-specific symptoms (e.g., for lung cancer: dyspnea, chest pain, hemoptysis and hoarseness).

The topotecan monohydrochloride pentahydrate and/or corresponding pharmaceutical compositions may be used in single agent therapy for any of the above-described treatments or uses or may be used in combination with other active treatment modalities such as radiation therapy, conventional anti-neoplastic agents, which include but are not limited to paclitaxel, docetaxel, doxorubicin, ara-c (cytarabine),5-fluorouracil, etoposide and organometallic coordination compounds, such as cisplatin and carboplatin and targeted biologic therapeutic approaches, which include but are not limited to, gefitinib, eriotinfD, lapatinib, bortezimib, elacridar, and erbitux.

The term "effective amount" means that amount of the topotecan monohydrochloride pentahydrate and/or a pharmaceutical composition containing the same, that upon administration to a mammal (such as a human being), in need thereof, provides a clinically desirable result in the treatment of various diseases, i.e., such as virally-related and/or cancer diseases (i.e., the latter of which may include anti-neoplastic treatment, which includes, but not limited to, tumor cell growth inhibition, remission, cure, amelioration of symptoms, etc.).

It will be appreciated that the actual preferred course of therapy will vary according to, inter alia, the particular formulation of the topotecan monohydrochloride pentahydrate being utilized, the mode of administration and the particular host being treated. An optimal therapy course for a given set of conditions may be ascertained by those skilled in the art using conventional course of therapy determination tests in view of the information set out herein and the disclosures of U.S. Pat. Nos. 5,004,758, 5,633,016, 5,674,872, and 5,756,512.

It will be appreciated that the actual preferred dosages of the compound used in the compositions and methods of treatment of the present invention will vary according to the particular composition formulated, the mode of administration and the particular site, such as host and tumor type being treated, etc. Moreover, optimal dosages for a specific pathological condition in a particular patient may ascertained by those of ordinary skill in the art, such as in the anti-viral or anti-neoplastic arts, using conventional dosage determination tests in view of the experimental data. In accordance with the present invention, components of each pharmaceutical composition and selection of the suitable one or more pharmaceutically acceptable carriers therefore, will depend upon the treatment effected and/or intended route of administration.

Another embodiment of this invention is directed to the use of the topotecan monohydrochloride pentahydrate of this invention to prepare of a wide variety of topotecan-containing pharmaceutical compositions, including solid forms (i.e., tablets, capsules, powders including lyophilized powders, etc.) or liquid forms (i.e., solutions, suspensions, or emulsions, etc.). Accordingly, a process for the preparation of such pharmaceutical compositions comprises using conventional art known materials and techniques, which may include, but are not limited to, mixing, blending and the like, of the topotecan monohydrochloride pentahydrate of this invention with one more pharmaceutically acceptable carriers.

The topotecan monohydrochloride pentahydrate, pharmaceutical compositions of the present invention and/or the topotecan-containing compositions may be administered by intravenous and intramuscular injection, parenterally, topically, orally, or by inhalation. The topotecan monohydrochloride pentahydrate, pharmaceutical compositions of the present invention and/or the topotecan-containing compositions may also be administered in injectable dosages by dissolution or suspension of these materials in a physiologically acceptable diluent with one or more pharmaceutically acceptable carriers.

Suitable pharmaceutically acceptable carriers, including adjuvants, diluents, excipients, surfactants and the like, contemplated for use in pharmaceutical compositions of the present invention include those known in the pharmaceutical formulary arts. For example, a reference to useful materials may be found in well-known pharmaceutical formulary compilation text books, such as Remington's Pharmaceutical Sciences (Mack Publishing Co., Easton, Pa.). Suitable carriers include, but are not limited to sterile liquids, such as water and oils, with or without the addition of a surfactant and/or other pharmaceutically and physiologically acceptable carriers, including adjuvants, excipients or stabilizers, etc. In general, liquid carriers, particularly as used in injectable solutions, may include, but are not limited to, water, saline, aqueous dextrose and related sugar solution, pharmaceutically acceptable glycols, such as propylene glycol or polyethylene glycol, and the like. Suitable oils for use in the present invention may include, but are not limited to petroleum, animal, vegetable oils, or oils of synthetic origin (e.g., peanut oil, soybean oil, hydrogenated vegetable oil or mineral oil, and the like). The pharmaceutical compositions may optionally contain a preservative to prevent the growth of microorganisms under ordinary conditions of storage and use.

If a liquid carrier is used, the pharmaceutical composition can be in the form of an emulsion, soft gelatin capsule, sterile injectable suspension or solution in an ampule or vial or nonaqueous liquid suspension.

If a desired pharmaceutical composition is in the form of a solution or suspension (which may also be encapsulated), examples of appropriate pharmaceutical carriers include: for aqueous systems, water; for non-aqueous systems: ethanol, glycerin, propylene glycol, vegetable oils (such as olive oil, corn oil, cottonseed oil, peanut oil, sesame oil, hydrogenated vegetable oil), liquid paraffins, glyceryl monostearate, mixtures thereof and mixtures thereof with water; for solid systems: lactose, terra alba, sucrose, talc, gelatin, agar, pectin, acacia, magnesium stearate, stearic acid, kaolin and mannitol; and for aerosol systems: dichlorodifluoromethane, chlorotrifluoroethane and compressed carbon dioxide.

The pharmaceutical compositions that may be prepared using the topotecan monohydrochloride pentahydrate of the present invention that are suitable for injectable use, may include, but are not limited to, sterile aqueous solutions or dispersions and sterile powders for extemporaneous preparation (reconstitution) as sterile injectable solutions or dispersions and the like. The pharmaceutical compositions of this invention include sterile dispersions and/or sterile powders comprising the topotecan monohydrochloride pentahydrate of this invention where, prior to injection, such dispersions or powders are reconstituted (e.g., by dissolving in water, saline, etc.) to form a sterile injectable solution or dispersion. In all cases, each injectable/reconstituted solution/dispersion should be sterile and be fluid to the extent that easy syringability exists. The pharmaceutical forms should be stable under conditions of manufacture and storage, which should be preserved against contaminating action of microorganisms, such as bacteria and fungi. For example, a carrier may be a solvent or dispersion medium which may include, but is not limited to water, ethanol, polyol (e.g., glycerol, propylene glycol, and liquid polyethylene glycol), vegetable oils, suitable mixtures thereof, and the like.

For parenteral administration, an injectable topotecan-containing pharmaceutical composition may include, but is not limited to be in the form of a sterile injectable liquid, such as a reconstituted lyophilized formulation or an aqueous or non-aqueous liquid suspension, and the like. Suitable solutions or suspensions of active compounds of the present invention may be prepared in water suitably mixed with a surfactant, such as hydroxypropylcellulose. Suitable dispersions may also be prepared in, but not limited to glycerol, liquid polyethylene glycols, and oil mixtures thereof, and the like.

U.S. Pat. No. 5,814,335, U.S. Pat. No. 5,552,156, U.S. Pat. No. 5,837,282, U.S. Pat. No. 5,543,152, and U.S. Pat. No. 5,741,516, and U.S. Patent Publication No. 2002/0110586, No. 2002/0119990, No. 2004/0071768 and No. 2004/0170678 disclose liposomes and/or micelles that may be used with the topotecan monohydrochloride pentahydrate of this invention in the preparation of topotecan-containing liposomal and/or micellular injectable compositions. A variety of lipids are known in the art which may be used to generate such liposomes. Generally single-layered liposomes have one membrane and are defined as "unilamellar". Multilayer liposomes are referred to as "multilamellar." Suitable lipids include, but are not limited to, neutral and negatively charged phospholipids or sphingolipids and sterols, such as cholesterol. Specific liposome compositions comprise various ratios of sphingomyelin and cholesterol. Other lipids also may be included in such liposome compositions as may be necessary, such as to prevent lipid oxidation or to attach ligands onto the liposome surface. Such liposomal topotecan-containing compositions may also be lyophilized (as in PCT/US2004/020592, the disclosure of which is incorporated herein by reference).

Particularly, the topotecan monohydrochloride pentahydrate may be used to prepare sterile, lyophilized formulations, suitable for parenteral administration, after reconstitution with (dissolution in) water or saline. One embodiment of this invention is directed to a process for the preparation of a lyophilized composition comprising, topotecan hydrochloride, mannitol, and tartaric acid, wherein the process comprises the steps of forming an aqueous solution mixture by dissolving the topotecan monohydrochloride pentahydrate of this invention, mannitol and tartaric acid in water, and lyophilizing the solution mixture to form a solid mixture. Optionally, prior to lyophilization, the pH of the solution mixture may be adjusted to about 2.5 to about 3.5. In addition, the solution mixture may optionally be placed in vials prior to lyophilization. After lyophilization, the resulting solid mixture may be sealed within the vials to maintain the mixture as a sterile powder.

The topotecan monohydrochloride pentahydrate of this invention or topotecan hydrochloride (Hycamtin) is administered in dosages based on the weight of topotecan free base (molecular weight: 421.4), not on the weight of topotecan monohydrochloride pentahydrate (molecular weight: 548.0) or topotecan monohydrochloride (molecular weight: 457.9). For example, a 4 mg dose of topotecan is provided by 4.35 mg of topotecan monohydrochloride.

For parenteral administration, a course of therapy generally employed is from about 0.5 mg topotecan/$m^2$ to about 25 mg topotecan/$m^2$ of body surface area per day for about one day to about seven consecutive days. In one embodiment, the course of therapy employed for a patient is from about 0.75 mg topotecan/$m^2$ to about 2 mg topotecan/$m^2$ of body surface area per day for about five to seven consecutive days. In another embodiment, the course of therapy employed is about 1.5 mg topotecan/$m^2$ of body surface area per day for about five consecutive days. The course of therapy may be repeated at least once at about a seven day to about a twenty-eight day interval (from the date of initiation of therapy) depending upon the initial dosing schedule and the patient's recovery of normal tissues. In one embodiment, the course of therapy may be repeated at 21 day intervals. If the topotecan monohydrochloride pentahydrate is used in a combination therapy (e.g., in some combination dosing with cisplatin, carboplatin, etoposide, paclitaxel or docetaxel), the amount of topotecan monohydrochloride pentahydrate may be reduced (e.g., by about 0.25-0.5 mg topotecan/$m^2$ of body surface area per day, or potentially more), depending on the needs and/or tolerance of the therapy by the patient. Other useful dosing regimens suitable for use with the topotecan monohydrochloride pentahydrate of this invention are possible.

The course of parenteral therapy may be repeated based on tumor response in cancer related diseases. The parenteral administration may be by short (e.g., 30 minute) or prolonged (e.g., 24-72 hour) intravenous infusion. Generally, the injectable topotecan-containing pharmaceutical compositions may be administered by a 30 minute intravenous infusion. For continuous intravenous administration, the dose that may be employed is about 0.5 mg topotecan/$m^2$/day for 5 days to 21 days.

For topical administration, a compound and/or pharmaceutical composition of the present invention may include, but is not limited to be in a form of a cream, ointment, liniment, lotion, paste, spray or drops suitable for administration to the skin, eye, ear, nose or genitalia and the like.

If a solid carrier is used, the preparation can be tableted, placed in a hard gelatin capsule in powder or pellet form or in the form of a troche or lozenge. In addition, solid carriers can be used to formulate compositions that can be inhaled. The amount of solid carrier will vary widely but preferably will be from about 25 mg to about 1 gram.

Suitable formulations for administration by inhalation include fine particle dusts or mists which may be generated by means of various types of metered dose pressurized aerosols, nebulisers, or insufflators. For pulmonary administration via the mouth, the particle size of the powder or droplets is typically in the range 0.5-10 µM, preferably 1-5 µM, to ensure delivery into the bronchial tree. For nasal administration, a particle size in the range 10-500 µM is preferred to ensure retention in the nasal cavity. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, surfactants.

For oral administration, the pharmaceutical compositions of the present invention and/or the topotecan-containing compositions may be in a form that includes, but is not limited to, a tablet, capsule, powder, pellet, troche, lozenge, syrup, suspension, elixir, liquid, or emulsion and/or other solid unit dosage forms as conventionally known in the art and the like. For example, the topotecan monohydrochloride pentahydrate, pharmaceutical compositions of the present invention and/or the topotecan-containing compositions may be orally administered with an inert carrier, an assimilable edible carrier, enclosed in hard or soft-shell capsules, compressed into tablets, and/or incorporated directly with food, etc. In one embodiment, the pharmaceutical composition of this invention, comprising the crystalline topotecan monohydrochloride pentahydrate described hereinabove, is in the form of a solid, orally administrable tablet or capsule.

The solubility of the topotecan monohydrochloride pentahydrate described herein may facilitate provision or development of a dosage form from which the drug substance (topotecan) becomes better available for bioabsorption. As a result, it may be possible to develop stable controlled release dosage forms, particularly oral dosage forms, which contain the topotecan monohydrochloride pentahydrate and/or corresponding pharmaceutical compositions of the present invention, for once-per-day dosage, controlled or delayed release or pulsatile release regiments, etc., to optimize therapy by matching pharmacokinetic performance with pharmacodynamic requirements. Alternatively, the dosage form (a pharmaceutical composition of this invention or a topotecan-containing composition) may be administered in combination with or may contain a compound that improves the bioavailability of the topotecan. Examples of compounds that may improve the bioavailability of topotecan are described in PCT/NL00/00331, published as WO00/69390, the disclosure of which is incorporated herein by reference.

A solid form suitable for use in the present invention may include, but is not limited to a capsule (i.e., such as an ordinary gelatin type) containing the topotecan monohydrochloride pentahydrate of this invention and one or more pharmaceutically acceptable carriers. Conventional pharmaceutically acceptable carriers that may be useful in the pharmaceutical compositions described herein include, but are not limited to lactose, sucrose, or cornstarch and the like, binders (i.e., such as acacia, gum, tragacanth, cornstarch, or gelatin, etc.), excipients (i.e., such as dicalcium phosphate), disintegrating agents (i.e., such as cornstarch, potato starch, or alginic acid), lubricants, (i.e., such as stearic acid, magnesium stearate, etc.); surfactants (i.e., sodium lauryl sulfate, sodium dodecyl sulfate and glyceryl monostearate) and a sweetening agent (i.e., such as sucrose, lactose, or saccharin, etc.). Various other materials may be present as coatings or to modify physical forms of each dosage unit. For instance, tablets may be coated with materials, which may include, but are not limited to shellac and/or, sugar, a syrup (i.e., which may include, but is not limited to an active ingredient, a sweetening agent (i.e., such as sucrose), preservatives (i.e., such as methyl and propylparabens), a dye, and flavorings (i.e., such as cherry or orange flavors), and the like. When the dosage unit form used is a capsule, it also may contain a liquid carrier (i.e., such as a fatty oil), etc. The pharmaceutically acceptable carrier may also include one or more materials that can provide a delayed release of the topotecan monohydrochloride pentahydrate. Such delayed-release materials are well known in the art and include glyceryl monostearate or glyceryl distearate alone or with a wax, ethylcellulose, hydroxypropylmethylcellulose, methylmethacrylate and the like. A specific embodiment of a pharmaceutical composition of this invention is a hard gelatin capsule encapsulating a dispersion of the topotecan monohydrochloride pentahydrate of this invention in a mixture of glyceryl monostearate and hydrogenated vegetable oil.

For oral administration of the topotecan monohydrochloride pentahydrate of this invention, the course of therapy generally comprises administration of a single dose of the topotecan monohydrochloride pentahydrate, wherein the dosage is from about 0.5 mg topotecan/$m^2$ to about 25 mg topotecan/$m^2$ of body surface area per day for about one to twenty-one consecutive days with courses of treatment repeated at appropriate intervals. In one embodiment, the course of therapy employed for oral administration is generally from about 1 mg topotecan/$m^2$ to about 2 mg topotecan/$m^2$ of body surface area per day for about five consecutive days. Generally, the course of therapy is repeated at least once at about a seven day to about a twenty-eight day interval (from the date of initiation of therapy) depending upon the initial dosing schedule and the patient's recovery of normal tissues. The course of therapy may be repeated based on tumor response. In one embodiment, the course of therapy may be repeated at 21 day intervals. Other useful dosing regimens suitable for use with the topotecan monohydrochloride pentahydrate of this invention are possible.

The Examples set forth below are illustrative of the present invention and are not intended to limit, in any way, the scope of the present invention.

EXAMPLE 1

Preparation of Topotecan Monohydrochloride Pentahydrate

Topotecan hydrochloride (2.9 g) is suspended in a mixture of acetone (23.2 mL, 8 volumes) and 0.05 N HCl (11.6 mL, 4 volumes). The aforementioned reaction mixture is heated to 58° C. to dissolve the solid topotecan hydrochloride. The reaction mixture solution is cooled, which results in the formation of a topotecan monohydrochloride pentahydrate slurry. The topotecan monohydrochloride pentahydrate crystallizes at 37° C. The slurry is cooled further to room temperature whereupon the reaction product, the crystalline topotecan monohydrochloride pentahydrate, is isolated by filtration and is dried.

EXAMPLE 2

Preparation of Topotecan Monohydrochloride Pentahydrate

Topotecan monohydrochloride (6.00 kg) was dissolved in a mixture of acetone (50.4 L, 8.4 volumes) and 0.05 N HCl (26.1 L, 4.4 volumes) by heating to 58° C. The resulting solution was cooled at a rate of about 1° C./min, with stirring, to 40° C., seeded with topotecan monohydrochloride pentahydrate seed material (5.9 g), and held at 35° C. for 1 h, during which time crystallization occurred. The resulting slurry was cooled to 0° C. at a rate of about 0.25° C./min. The reaction product, topotecan monohydrochloride pentahydrate, was isolated by filtration and dried at 32° C. and −0.76 barG for 62 hours while passing a vigorous stream of nitrogen through the vessel. Yield 4.597 kg of yellow powder.

This procedure produces the topotecan monohydrochloride pentahydrate of this invention with or without the step of seeding the solution with topotecan monohydrochloride pentahydrate seed material.

EXAMPLE 3

X-Ray Diffraction and FT-Infrared Data for Topotecan Monohydrochloride Pentahydrate X-Ray Diffraction, General Procedure The x-ray powder diffraction pattern for the topotecan monohydrochloride pentahydrate, that is prepared according to the procedure of Example 1 or Example 2, is recorded or scanned using a Philips X'Pert Pro Diffractometer instrument, where the following sample preparation procedures and/or techniques are used to obtain the x-ray diffraction pattern with the following acquisition parameters.

The sample is spiked with a few milligrams of Si powder (internal standard), and mixed in a mortar and pestle. Approximately 30 mg of the sample is gently flattened on a zero background silicon sample holder. The holder is placed into a designated position in the 15-position sample magazine and the computer is programmed with the correct sample information immediately to prevent sample position mix up. The sample containing the topotecan monohydrochloride pentahydrate is scanned using the instrument or acquisition parameters provided in Table 1.

TABLE 1

X-Ray Diffraction Acquisition Parameters for Crystalline Topotecan Monohydrochloride Pentahydrate

| | |
|---|---|
| Scan range: | 2 degrees two-theta to 35 degrees two-theta |
| Generator power: | 40 kV, 40 mA |
| Radiation Source: | Cu K-alpha |
| Scan type: | Continuous |
| Step Time: | 10.160 seconds |
| Sample Rotation: | 25 rpm |
| Step Size: | 0.0167 degrees two-theta per step |
| Incident Beam Optics: | fixed slits (0.5 degree aperture), 0.04 radian soller slits, 10 mm beam mask |
| Diffracted Beam Optics: | fixed slits (X'celerator module), 0.04 radian soller slits |
| Detector Type: | Philips X'Celerator RTMS (Real Time Multi Strip) |

The X-ray powder diffraction pattern obtained for a sample of the topotecan monohydrochloride pentahydrate according to this invention is shown in FIG. 1. The diffraction angles (° 2θ) and d-spacings (Angstroms) calculated from the acquisition data are provided in Table 2.

TABLE 2

X-Ray Diffraction Data for Topotecan Monohydrochloride Pentahydrate (Diffraction Angles (°2θ) and D-Spacings (Angstroms))

| Diffraction angle (°2θ)* | D-spacing (Angstroms) |
|---|---|
| 4.5 | 19.7 |
| 6.4 | 13.8 |
| 7.1 | 12.4 |
| 9.0 | 9.8 |
| 10.1 | 8.8 |
| 11.5 | 7.7 |
| 12.6 | 7.0 |
| 13.1 | 6.7 |
| 14.1 | 6.3 |
| 15.5 | 5.7 |
| 17.9 | 5.0 |
| 18.7 | 4.7 |
| 20.0 | 4.4 |
| 20.3 | 4.4 |
| 21.1 | 4.2 |
| 21.8 | 4.1 |
| 23.0 | 3.9 |
| 24.8 | 3.6 |
| 25.6 | 3.5 |
| 26.6 | 3.3 |
| 27.2 | 3.3 |
| 28.9 | 3.1 |

*Using copper K-alpha 1 radiation.

Infra Red, General Procedure:

The sample for FT-IR analysis is prepared by diluting approximately 2 mg of a sample of the topotecan monohydrochloride pentahydrate of this invention with 300 mg of dried potassium bromide (KBr). The resulting mixture is subjected to grinding with a mortar and pestle, then transferred to a die that is placed under high pressure for 3 minutes. At least 100 scans are collected using a FT-IR spectrometer equipped with a dTGS detector at 4 cm$^{-1}$ resolution.

Figure 2:
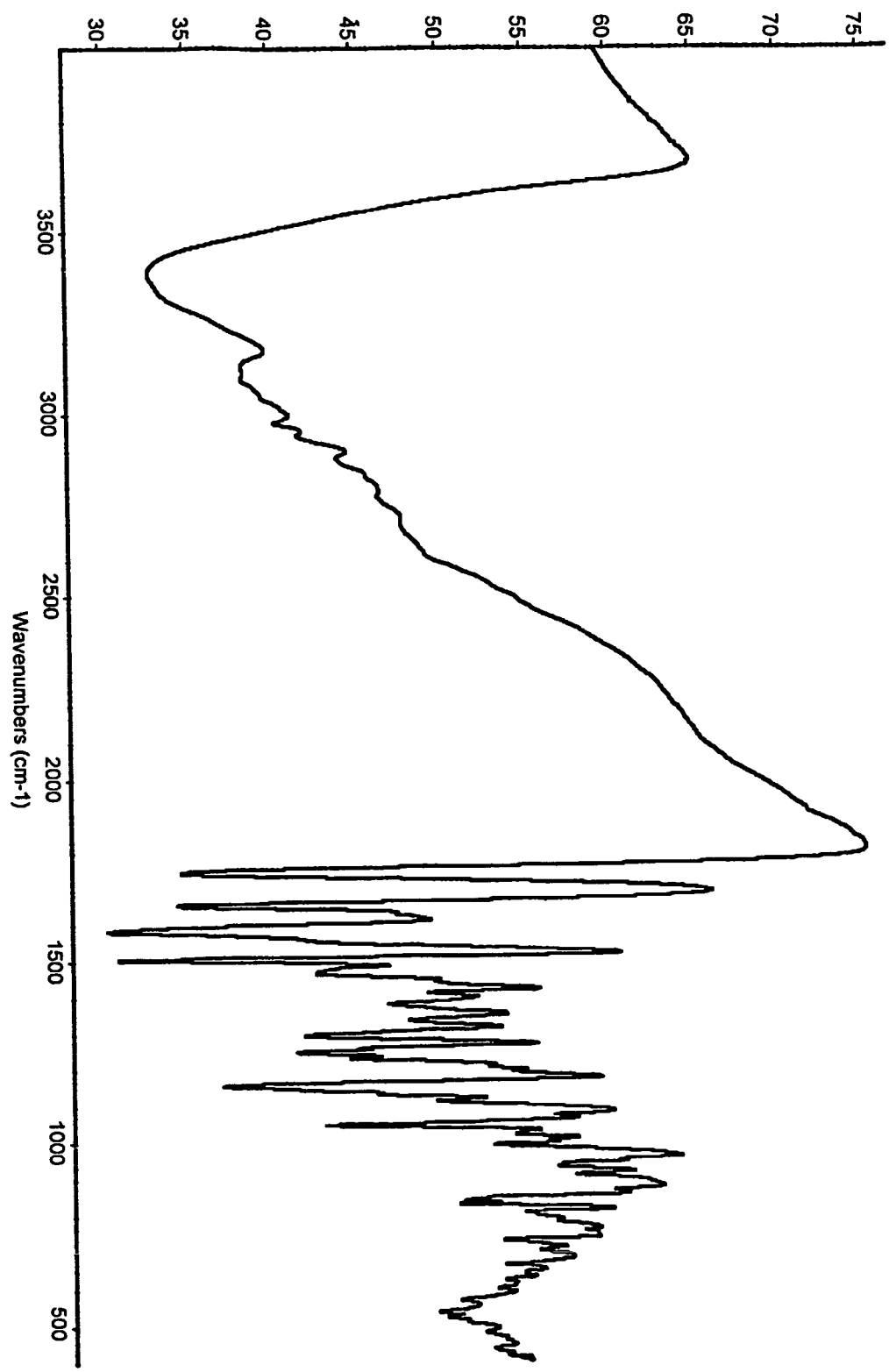
FIG. 2 is a FT-IR (KBr) spectrum of a topotecan monohydrochloride pentahydrate polymorphic form.

The full range spectrum for the topotecan monohydrochloride pentahydrate crystal form of this invention may vary somewhat in the region from 3700 cm$^{-1}$ to 2500 cm$^{-1}$ due to varying levels of water present in the sample. A full range FT-IR spectrum obtained for a sample of the topotecan monohydrochloride pentahydrate according to this invention is shown in FIG. 2.

The second derivative spectrum (or the inverse second derivative spectrum) of the IR region from 1800 cm$^{-1}$ to 1500 cm$^{-1}$ may be used for characterization of the crystalline form. This spectrum can be obtained by converting the ordinate scale to absorbance units, expanding the spectral region of 1800 cm$^{-1}$ to 1500 cm$^{-1}$, and taking a second derivative of the resulting spectrum. The second derivative spectrum is multiplied by a factor of negative one to produce an inverse second derivative spectrum. FIG. 3 illustrates the inverse second derivative spectrum for the spectral region of 1800 cm$^{-1}$ to 1500 cm$^{-1}$ for the topotecan monohydrochloride pentahydrate of this invention. The characteristic IR bands for the topotecan monohydrochloride pentahydrate of this invention appear at approximately 1754 cm$^{-1}$, 1745 cm$^{-1}$, 1740 cm$^{-1}$, 1658 cm$^{-1}$, 1649 cm$^{-1}$, 1596 cm$^{-1}$ 1584 cm$^{-1}$, and 1507 cm$^{-1}$ (with an experimental variation of ±2 cm$^{-1}$). In some cases, the characteristic bands appear as shoulders. The presence of a shoulder at one or more of the above-identified positions is satisfactory for confirmation of identity.

The above description fully discloses how to make and use the present invention. However, this invention is not limited to the particular embodiments described hereinabove, but includes all modifications thereof within the scope of the appended claims and their equivalents. Those skilled in the art will recognize through routine experimentation that various changes and modifications can be made without departing from the scope of this invention, such that the right is reserved to illustrated embodiments and all modifications coming within the scope of the following claims. Each of the various patents, patent applications and patent application publications that are cited herein are incorporated by reference herein in their entirety, as though fully set forth.

What is claimed is:

1. A topotecan monohydrochloride pentahydrate product having an X-ray powder diffraction pattern that is substantially the same as FIG. 1.

2. A topotecan monohydrochloride pentahydrate product having an inverse second derivative FT-IR spectrum for the spectral region of 1800 cm$^{-1}$-1500 cm$^{-1}$ that is substantially the same as FIG. 3.

3. The product according to claim 1, wherein the product has a water content range between from about ≧10% w/w % to about ≦17 w/w %.

4. The product according to claim 1, wherein the product has a water content in a range of about 10.5 wt % to about 16.5 wt %.

5. The topotecan monohydrochloride pentahydrate product having an X-ray diffraction pattern that is substantially the same as FIG. 1,
wherein the product is prepared by a process comprising the steps of:
 [a] forming an aqueous organic solvent mixture containing topotecan monohydrochloride, wherein the organic solvent of the aqueous organic solvent mixture is selected from the group consisting of acetone and tetrahydrofuran, and wherein the ratio of organic solvent to aqueous solvent in the aqueous organic solvent mixture is from about 1.5:1 to about 3:1;
 [b] recrystallizing the topotecan monohydrochloride from the aqueous organic solvent mixture to precipitate the topotecan monohydrochloride pentahydrate product; and
 [c] collecting, by filtration, the topotecan monohydrochloride pentahydrate product.

6. The product according to claim 5, wherein the aqueous organic solvent mixture comprises an aqueous mineral acid solution.

7. The product according to claim 5, wherein the aqueous mineral acid solution is a 0.05 N aqueous hydrochloric acid solution.

8. The product according to claim 5, wherein the aqueous organic solvent mixture comprises a mixture of acetone and a 0.05 N aqueous hydrochloric acid solution.

9. The product according to claim 5, wherein process step [b] comprises recrystallizing the topotecan monohydrochloride from the aqueous organic solvent mixture which comprises acetone and 0.05 N aqueous hydrochloric acid, wherein the v/v ratio of acetone to aqueous hydrochloric acid is about 2:1.

10. The product according to claim 5, prepared by a process further comprising the steps of:
 first dissolving topotecan monohydrochloride in a heated aqueous organic solvent solution mixture;
 crystallizing or recrystallizing the topotecan monohydrochloride pentahydrate from the heated solution by cooling the solution; and
 filtering the resulting recrystallized topotecan monohydrochloride pentahydrate product and drying.

11. The product according to claim 10, wherein the heated aqueous organic solvent solution mixture is a mixture of acetone and 0.05 N aqueous hydrochloric acid heated to a temperature of about 58° C. and the v/v ratio of acetone to aqueous hydrochloric acid is about 2:1.

12. The product according to claim 10, wherein the heated solution is cooled at a rate of about 0.1° C./min to about 1° C./min.

13. The product according to claim 10, wherein the heated solution is cooled at a rate of about 0.25° C./min.

14. The product according to claim 10, wherein, in the crystallization or recrystallization process, the solution is cooled to a temperature of about room temperature to about 0° C.

15. A topotecan monohydrochloride pentahydrate product having an X-ray diffraction pattern that is substantially the same as FIG. 1,
wherein the product is prepared by a process comprising the steps of:
[a] forming an aqueous organic solvent mixture containing topotecan monohydrochloride, wherein the aqueous solvent of the aqueous organic solvent mixture is an aqueous mineral acid solution, the organic solvent of the aqueous organic solvent mixture is selected from the group consisting of acetone and tetrahydrofuran, and wherein the v/v ratio of organic solvent to aqueous solvent is about 8:1;
[b] slurrying the topotecan monohydrochloride with the aqueous organic solvent mixture to form the topotecan monohydrochloride pentahydrate product; and
[c] collecting, by filtration, the topotecan monohydrochloride pentahydrate product.

16. The product according to claim 15, wherein the aqueous organic solvent mixture comprises a 0.05 N aqueous hydrochloric acid solution.

17. A process for preparing the product according to claim 1 comprising the steps of:
[a] forming an aqueous organic solvent mixture containing topotecan monohydrochloride, wherein the organic solvent of the aqueous organic solvent mixture is selected from the group consisting of acetone and tetrahydrofuran;
[b] recrystallizing the topotecan monohydrochloride from the aqueous organic solvent mixture to precipitate the topotecan monohydrochloride pentahydrate product; and
[c] collecting, by filtration, the topotecan monohydrochloride pentahydrate product.

18. The process according to claim 17, wherein the aqueous organic solvent mixture comprises an aqueous mineral acid solution.

19. The process according to claim 18, wherein the aqueous mineral acid solution is a 0.05 N aqueous hydrochloric acid solution.

20. The process according to claim 17, wherein the aqueous organic solvent mixture comprises a mixture of acetone and a 0.05 N aqueous hydrochloric acid solution.

21. The process according to claim 17, wherein step [b] comprises recrystallizing the topotecan monohydrochloride from the aqueous organic solvent mixture which comprises acetone and 0.05 N aqueous hydrochloric acid, wherein the v/v ratio of acetone to aqueous hydrochloric acid is about 2:1.

22. The process according to claim 17, further comprising:
first dissolving topotecan monohydrochloride in a heated aqueous organic solvent solution mixture;
crystallizing or recrystallizing the topotecan monohydrochloride pentahydrate from the heated solution by cooling the solution; and
filtering the resulting recrystallized topotecan monohydrochloride pentahydrate product and drying.

23. The process according to claim 22, wherein the heated aqueous organic solvent solution mixture is a mixture of acetone and 0.05 N aqueous hydrochloric acid heated to a temperature of about 58° C. and the v/v ratio of acetone to aqueous hydrochloric acid is about 2:1.

24. The process according to claim 22, wherein the cooling rate is in the range of about 0.1° C./min to about 1° C./min.

25. The process according to claim 22, wherein, in the crystallization or recrystallization process, the solution is cooled to a temperature of about room temperature to about 0° C.

26. A process for preparing the product according to claim 1 comprising the steps of:
[a] forming an aqueous organic solvent mixture containing topotecan monohydrochloride, wherein the aqueous solvent of the aqueous organic solvent mixture is an aqueous mineral acid solution, the organic solvent of the aqueous organic solvent mixture is selected from the group consisting of acetone and tetrahydrofuran, and wherein the v/v ratio of organic solvent to aqueous solvent is about 8:1
[b] slurrying the topotecan monohydrochloride with the aqueous organic solvent mixture to form the topotecan monohydrochloride pentahydrate product; and
[c] collecting, by filtration, the topotecan monohydrochloride pentahydrate product.

27. The process according to claim 26, wherein the aqueous organic solvent mixture comprises a mixture of acetone and a 0.05 N aqueous hydrochloric acid solution.

* * * * *